United States Patent [19]
Witt et al.

[11] Patent Number: 5,605,272
[45] Date of Patent: Feb. 25, 1997

[54] TRIGGER MECHANISM FOR SURGICAL INSTRUMENTS

[75] Inventors: David A. Witt, Loveland; Kirk M. Nicola, West Chester; Robert G. Cook, Mason; Joseph C. Hueil, Loveland; Richard W. Flaker, Fairfield, all of Ohio

[73] Assignee: Ethicon Endo-Surgery, Inc., Cincinnati, Ohio

[21] Appl. No.: 614,415

[22] Filed: Mar. 12, 1996

[51] Int. Cl.⁶ .................................................. A61B 17/068
[52] U.S. Cl. ........................................ 227/175.2; 227/19
[58] Field of Search .............................. 227/175.1, 175.2, 227/175.3, 176.1, 179.1, 181.1, 19, 8

[56] References Cited

U.S. PATENT DOCUMENTS 5,465,894  11/1995  Clark et al. ................................ 227/19

*Primary Examiner*—Scott A. Smith
*Attorney, Agent, or Firm*—Matthew S. Goodwin

[57] ABSTRACT

A linear surgical stapler having clamping and firing triggers pivotally mounted to the frame of the instrument for pivotal rotation toward a hand grip is disclosed. The clamping trigger is positioned between the firing trigger and the hand grip. Each of the triggers are pivotally mounted to pivot pins spaced from each other within the body portion of the frame. Pivotal rotation of the first trigger is independent of pivotal rotation of the second trigger. When the clamping trigger is pivotally rotated toward the hand grip, the clamping and firing transmission assemblies move distally in tandem. Before the first trigger is pivoted, the firing transmission assembly blocks pivotal rotation of the second trigger. When the first trigger is pivoted, the initial distal movement of the firing transmission assembly enables the firing trigger to be in a position to pivotally rotate, and therefore cause the firing of staples. Additionally, a feature enabling the retention of the clamping trigger in intermediate and fully clamped positions is disclosed, where upon release of the retention feature, the clamping trigger can return to its original position by overriding the intermediate position. Finally, although the invention is described with particular reference to a linear stapler containing clamping and firing triggers, it has broader applicability to any surgical instrument which has first and second triggers pivotally actuated to transmit work to an end effector for performing first and second surgical functions during a desired surgical procedure.

19 Claims, 10 Drawing Sheets

TRIGGER MECHANISM FOR SURGICAL INSTRUMENTS

BACKGROUND OF THE INVENTION

This invention relates to surgical instruments which have at least two triggers to actuate the business end of the instrument to manipulate bodily tissue. More specifically, it relates to surgical instruments which have a frame, and clamping and firing triggers mounted to the frame for causing the clamping of bodily tissue and the firing of staples into the clamped tissue at the business end of the instrument.

Surgical instruments typically include a frame for manipulating the instrument and an "end effector" remote from the frame at the business end of the instrument to cause the manipulation of bodily tissue in some desired fashion. Frequently, the actuation of the end effector to cause the manipulation of the tissue is carried out when the surgeon squeezes or depresses a trigger or lever mounted to the frame. In many surgical instruments, more than one trigger or lever mounted to the frame is necessary to effect the actuation of different functions which the end effector is designed to perform during the manipulation of the tissue. A classic example of where two triggers or levers mounted to the frame have been used is with surgical staplers.

One particular type of surgical stapler, frequently referred to as a "linear stapler", fires vertical rows of staples into bodily tissue. It has an end effector which includes a cartridge carrying a plurality of staples and an anvil upon which the staples are formed. The cartridge and anvil are movable relative to each other from an open position where tissue is placed between the cartridge and anvil to a closed position where the cartridge and anvil are adjacent to each other and the tissue positioned between them is clamped. A linear stapler can be particularly designed for applications involving minimally invasive surgery, where surgery is performed through small openings, or conventional "open" surgery.

Linear staplers have clamping and firing triggers or levers mounted to the frame of the stapler. When the surgeon squeezes or depresses the clamping trigger or lever, the bodily tissue positioned between the cartridge and anvil is clamped as the components of the end effector move to their closed position. Subsequently, the surgeon squeezes or depresses the firing trigger or lever to fire the staples from the cartridge against the anvil to staple the clamped tissue. Obviously, the way in which the clamping and firing triggers are mounted to the frame of the linear stapler has a significant impact on the operability and "feel" of the instrument from the surgeon's perspective. Additionally, the mounting affects the cost and reproducibility of the stapler for manufacturing on a commercial scale.

Excellent examples of preferred clamping and trigger mounting techniques for linear staplers are described in U.S. Pat. Nos. 5,307,976 and 5,452,836. These parents describe a linear stapler which has a frame and a hand grip handle descending from the frame for the surgeon to grip. The clamping and firing triggers likewise descend from the frame and are pivotally mounted to it for actuation. The clamping trigger is initially positioned so that the surgeon can grip the hand grip with the palm of his hand and extend his fingers to grasp the clamping trigger and squeeze it. Upon squeezing, the clamping trigger pivots counterclockwise towards the hand grip handle. In so doing, the firing trigger similarly pivots from its original position approximately 45° from the underside of the frame to an intermediate position located at about the position which represented the original position of the clamping trigger. Accordingly, once the surgeon has fully squeezed the clamping trigger and it is positioned adjacent to the hand grip handle, the surgeon is then in position to grasp and squeeze the firing trigger. This is an outstanding mechanism, but, of course, there is always room for improvement. Specifically, the pivotal movement of the clamping and firing triggers is dependent on each other. In other words, movement of the clamping trigger necessarily entails a corresponding movement of the firing trigger. Consequently, the clamping and firing triggers may require the use of precision parts to ensure precise movement of the triggers in tandem during operation, resulting in an increase in manufacturing costs and design complexity.

Another feature of a linear stapler which would be desirable is a feature which enables the surgeon to squeeze the clamping trigger into an intermediate or partially closed position. This feature would allow the surgeon to conveniently and properly position the stapler before full closure and stapling is accomplished. Once the positioning of the stapler is set, it would be desirable if the surgeon could then squeeze the clamping trigger from its partially closed position to its fully closed position for tissue clamping. Additionally, it would also be desirable if the clamping trigger of the stapler could be returned to its original fully opened position by overriding the partially closed position following the stapling of tissue.

Accordingly, it would be beneficial to develop a surgical instrument, particularly a linear stapler, which incorporates clamping and firing triggers which are pivotal toward a hand grip handle, but which are independent of each other for the pivotal movement. Furthermore, it would be beneficial to develop a stapler which has a clamping trigger capable of actuation to an intermediate or partially closed position. Ideally, it would be possible to override the partially closed position of the clamping trigger following the stapling of the tissue when opening the instrument.

SUMMARY OF THE INVENTION

The invention is a surgical instrument which has a frame, an end effector, first and second triggers, and first and second transmission assemblies. Each of these components of the instrument will now be broadly described.

The frame of the instrument is at a first end of the instrument. The frame is adapted for enabling the surgeon to grip and manipulate the instrument. The frame has a body portion and a hand grip descending from the body portion of the frame.

The end effector of the instrument is at an end opposite the frame. It is adapted for performing a desired surgical procedure.

The first trigger is pivotally mounted to a first pivot pin within the body portion of the frame. It pivotally rotates in a counterclockwise direction from an unactuated first trigger position spaced from the hand grip to a fully actuated first trigger position adjacent the hand grip.

The first transmission assembly has proximal and distal ends. The proximal end is operatively coupled to the first trigger, and the distal end of the first transmission assembly is operatively coupled to the end effector. When the first trigger is pivotally rotated in a counterclockwise direction toward the hand grip, the first transmission assembly moves distally to cause the end effector to perform a first surgical function in the desired surgical procedure.

The second trigger is pivotally mounted to a second pivot pin within the body portion of the frame. The second pivot pin is spaced from the first pivot pin. The second trigger pivotally rotates in a counterclockwise direction from an unactuated second trigger position spaced from the first trigger to a fully actuated second trigger position adjacent the first trigger. The pivotal rotation of the second trigger is independent of the pivotal rotation of the first trigger. Additionally, the first trigger is positioned between the second trigger and the hand grip.

The second transmission assembly also has proximal and distal ends. The proximal end of the second transmission assembly is engagable with the second trigger, and the distal end of the second transmission assembly is engagable with the end effector. When the first trigger is positioned in its unactuated first trigger position, the proximal end of the second transmission assembly blocks the pivotal rotation of the second trigger in a counterclockwise direction from its unactuated second trigger position toward the first trigger. However, when the first trigger is pivotally rotated in a counterclockwise direction from its unactuated first trigger position toward the hand grip, the second transmission assembly moves distally concurrently with the first transmission assembly until the proximal end of the second transmission assembly no longer blocks the second trigger from pivotally rotating in the counterclockwise direction. Consequently, when the first trigger is pivotally rotated to its fully actuated trigger position, pivotal rotation of the second trigger in a counterclockwise direction toward the first trigger continues to move the second transmission assembly distally to cause the end effector to perform a second surgical function in the desired surgical procedure.

The invention represents a multifunctional surgical instrument which incorporates numerous enhanced features providing benefits for the surgeon and the manufacturer. It takes advantage of first and second pivotally mounted triggers which the surgeon can sequentially squeeze against a hand grip to perform various surgical functions during a desired surgical procedure. However, it utilizes this advantage to create an instrument which is ergonomically ideal for the surgeon, without the disadvantages associated with an increase in manufacturing costs and design complexity because of the need for precision parts to ensure precise movement of the triggers in tandem. Significantly, instead of having the first and second triggers dependent on each other for pivotal rotation, the first and second triggers of the surgical instrument of this invention can pivotally rotate independently of each other. Therefore, it is unnecessary to engineer precision trigger components to ensure that rotation of the first trigger causes a precise required rotation of the second trigger.

Advantageously, the second trigger is blocked from pivotally rotating toward the hand grip until the first trigger has been squeezed toward the hand grip. With the features of this invention, it is unnecessary to link the pivotal rotation of the first trigger with the second to prevent the second trigger from rotating prematurely, but rather the second trigger is blocked from rotating until the first trigger moves the second transmission assembly distally. In so doing, the first and second triggers can be manufactured relatively independently, and overall costs can be reduced.

In the preferred embodiment of this invention, the first transmission assembly includes a pair of closure plates which, when the first trigger is pivotally rotated toward the hand grip, cause a surgical fastening assembly at the end effector to clamp tissue between a cartridge and an anvil. Correspondingly, the second transmission assembly preferably includes an elongated firing bar which, when the second trigger is pivotally rotated toward the first trigger, fires staples into tissue clamped between the cartridge and anvil of the surgical fastening assembly of the end effector.

In a particularly preferred embodiment when the end effector includes a surgical fastening assembly, the clamping trigger can be retained in an intermediate, tissue retention position where tissue can be properly positioned between the cartridge and anvil of the surgical fastening assembly of the end effector. In addition, the clamping trigger can be retained in its fully actuated first trigger position adjacent the hand grip. When so retained, tissue placed between the cartridge and anvil is fully clamped. To accomplish this function, a release pall, a sliding surface on a clamping arm link, and an intermediate detent and a final clamping detent are featured on the instrument. The pall lodges into the intermediate and final detents to correspondingly retain the clamping trigger in the intermediate and fully clamped positions, respectively. The pall engages a toggle, which has a toggle arm, and rotates the toggle in a first direction. The toggle arm enables the pall to ride over the final detent, disengage from the arm, and then subsequently lodge into the clamping detent for full clamping. When the surgeon desires to release the fastened tissue from the cartridge and anvil of the surgical fastening assembly, he can then depress a release button attached to the pall, and consequently dislodge the pall from the final detent. As the clamping trigger returns from its fully actuated position adjacent the hand grip toward its unactuated position, the pall reengages the arm of the toggle and rotates it in the opposite direction. As the pall causes the toggle arm to rotate, it enables the pall to ride over the intermediate detent as the first trigger returns to its original, unactuated position. Significantly, the interaction between the pall and the toggle arm enables the clamping trigger to override the intermediate tissue retaining position when it returns to its original position.

The surgical instrument of this invention can be used in any surgical procedure, whether endoscopic or conventional open procedures, where it is desirable or necessary to perform first and second surgical functions in a particular surgical procedure. This instrument, however, is particularly adapted when a first surgical function to be performed is to clamp tissue, and a second surgical function to be performed is to fire staples into the clamped tissue. Ideally, the surgical instrument of this invention is utilized as a linear stapler.

DETAILED DESCRIPTION OF THE PREFERRED EMBODIMENT

Figure 1:
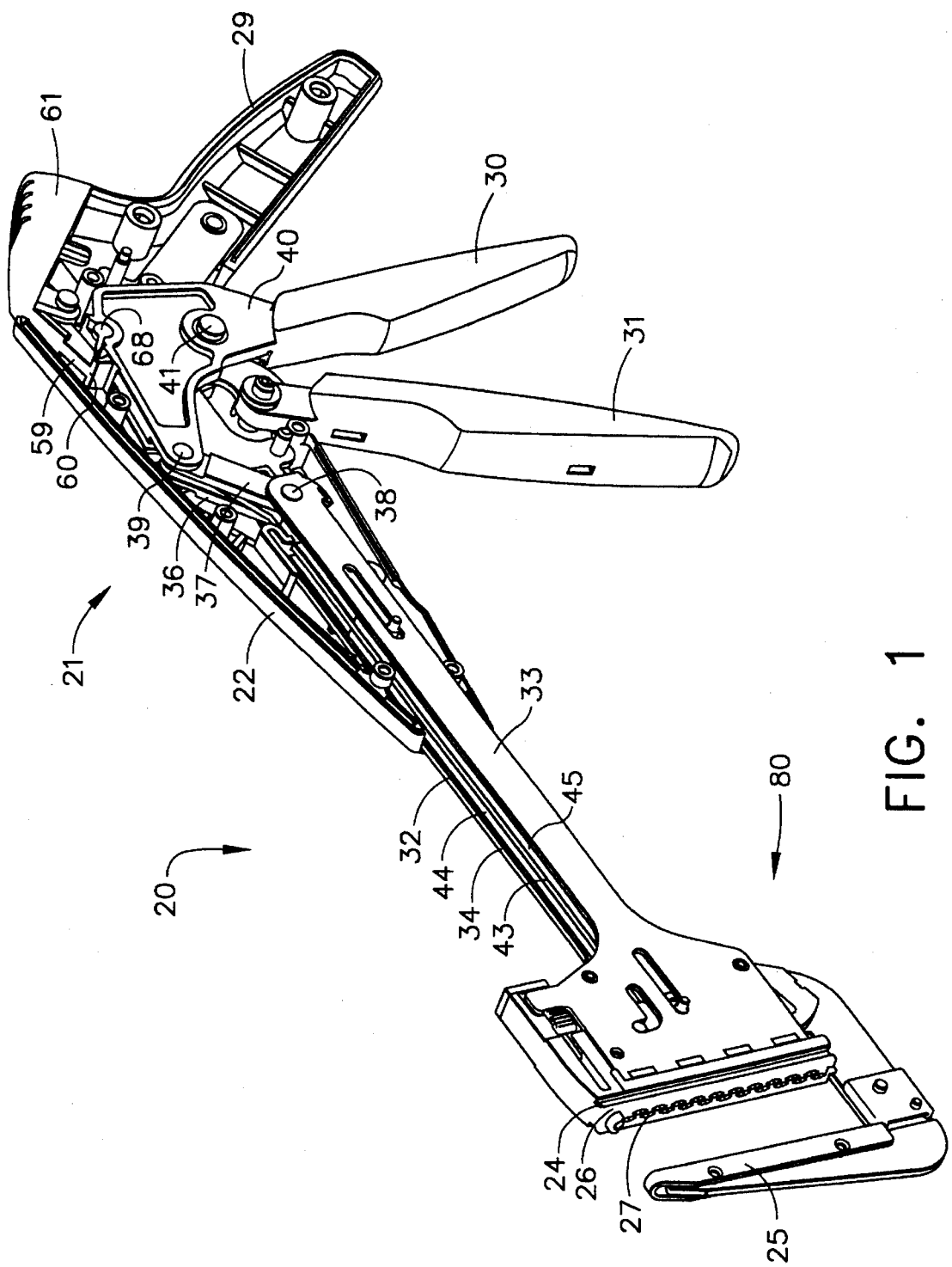
FIG. 1 is an isometric view of a preferred embodiment of this invention in the form of a surgical linear stapler with the left hand shroud and the left hand structural plate (often referred to the "hook") removed to expose the internal components of the stapler. Four operating springs have also been removed for clarity.
Figure 2:
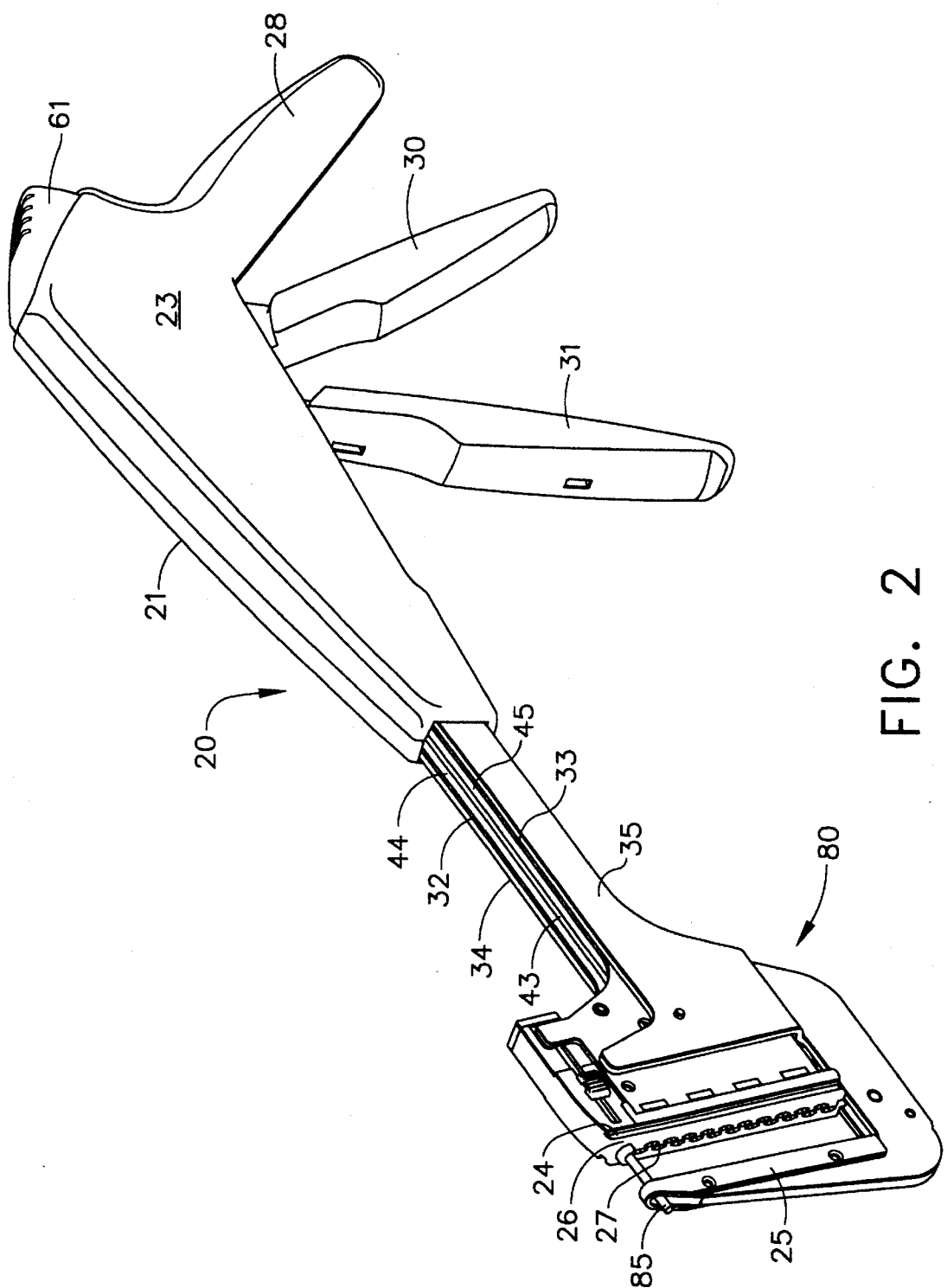
FIG. 2 is an isometric view of the surgical linear stapler of FIG. 1 in which the end effector of the stapler is positioned in the partially clamped or tissue retention position.
Figure 3:
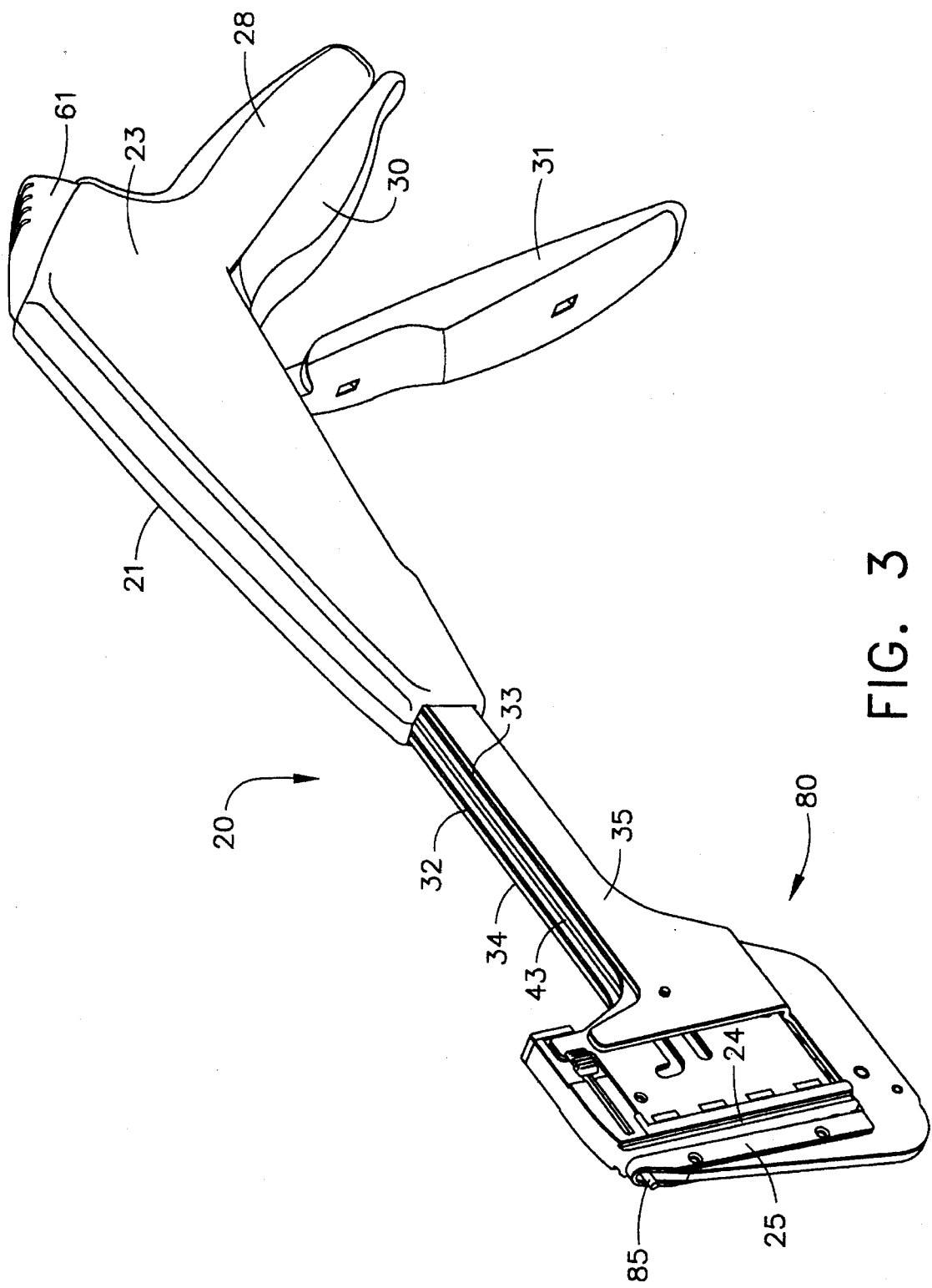
FIG. 3 is an isometric view of the surgical linear stapler of FIG. 1 in which the end effector of the stapler is positioned in the clamped position for fully clamping tissue.
Figure 4:
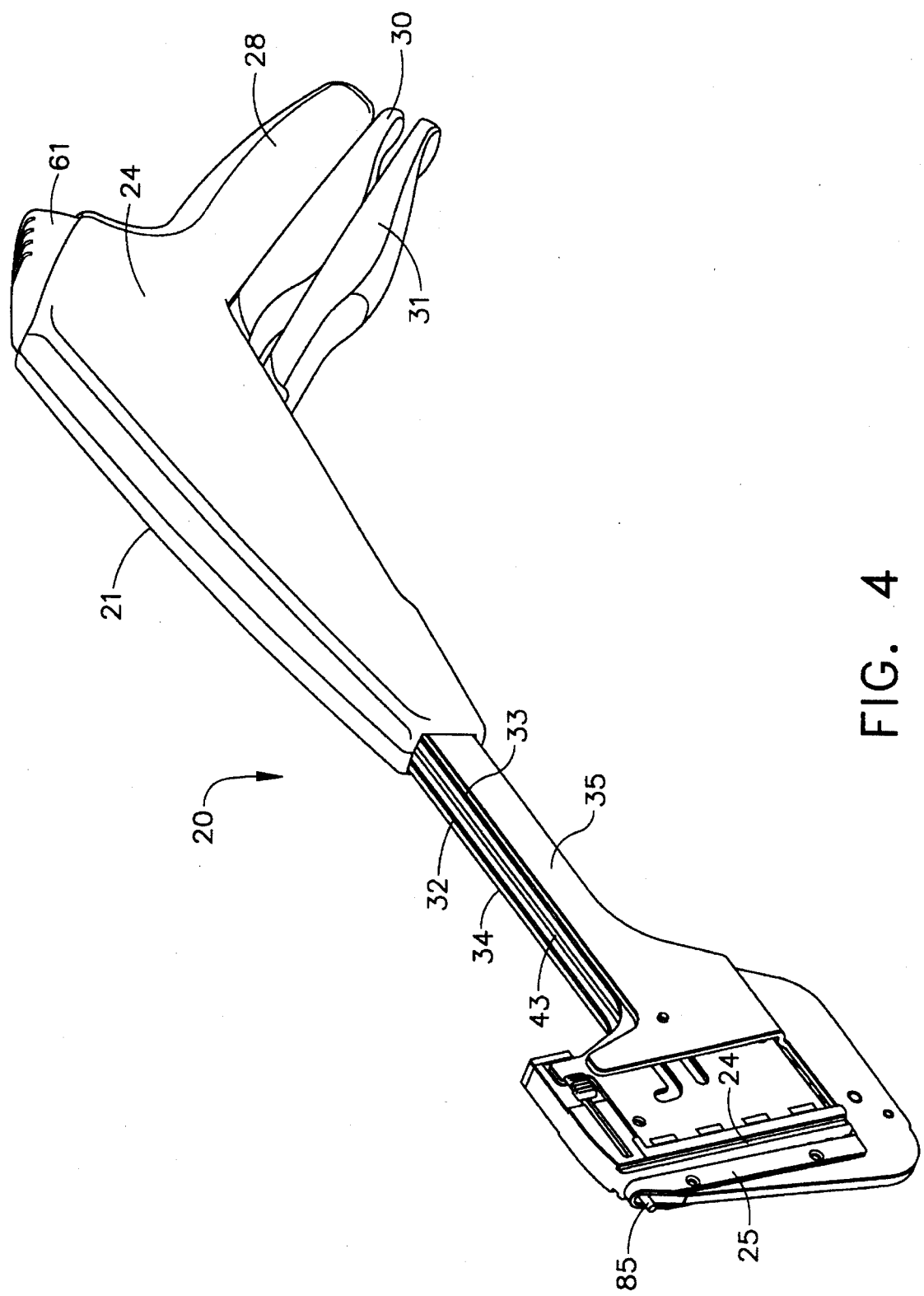
FIG. 4 is an isometric view of the surgical linear stapler of FIG. 1 in which the end effector of the stapler is positioned in the fired position where staples have been fired from the cartridge against the anvil of the surgical fastening assembly of the end effector.

Referring to FIG. 1 in combination with FIGS. 2–4, there is shown a linear surgical stapler 20. The stapler has a frame 21 at a first proximal end and an end effector 80 at an opposite distal end. Right and left hand structural plates, or hooks, 34 and 35, respectively, connect the frame to the end effector of the instrument (the left hand hook is not shown in FIG. 1). The frame has a right hand shroud 22 coupled to a left hand shroud (the left hand shroud is not shown in FIG. 1). The frame also has a body portion 23 to grip and maneuver the stapler (see FIGS. 2–4). The end effector is a surgical fastening assembly which has a cartridge 24 and an anvil 25. The cartridge has a tissue contacting surface 26 which displays a plurality of staple-containing slots 27 in vertical rows. Staples (not shown) are fired from the cartridge against the staple-forming surface of the anvil (not shown) which faces the tissue-contacting surface of the cartridge.

The frame of the stapler includes a hand grip 28 which the surgeon grasps with the palm of his hand (see FIGS. 2–4). The hand grip is formed from the coupling of the right hand shroud handle 29 (see FIG. 1) to the left hand shroud handle (the left hand shroud handle is not shown in FIG. 1). Pivotally extending from the underside of the frame are a closure trigger 30 and a firing trigger 31. The linear surgical stapler illustrated in FIG. 1 is shown with the clamping and firing triggers in their unactuated positions. Consequently, the cartridge is spaced from the anvil for the placement of tissue between the cartridge and anvil.

Referring briefly to FIGS. 2–4, there is illustrated what happens when the clamping and firing triggers are sequentially squeezed toward the hand grip to actuate the end effector of the linear stapler. When the clamping trigger is partially squeezed to rest in its first detent position shown in FIG. 2, the cartridge moves from its fully opened position to an intermediate position between the open and closed positions. Simultaneously, a tissue retaining pin 85 moves forwardly from the cartridge through an opening in the anvil. In this position, tissue which has been placed between the cartridge and anvil can be properly positioned, and the retention of the tissue between the cartridge and anvil can be assured. Therefore, when the clamping trigger has been actuated to its intermediate position, the cartridge and anvil are correspondingly positioned in their tissue retaining positions. When the clamping trigger is fully squeezed so that it is adjacent the forward end of the handle grip as illustrated in FIG. 3, the tissue-contacting surface of the cartridge and the staple-forming surface of the anvil are adjacent to each other, and the properly positioned and retained tissue is consequently fully clamped. Additionally, the firing trigger has rotated counterclockwise toward the handle grip to enable the surgeon to grasp the firing trigger for the firing of staples. Accordingly, the firing trigger is now in position for the surgeon to squeeze it to staple the tissue. When the firing trigger has been fully squeezed to fire the staples, as shown in FIG. 4, the firing trigger rests in near proximity to the clamping trigger.

Figure 5:
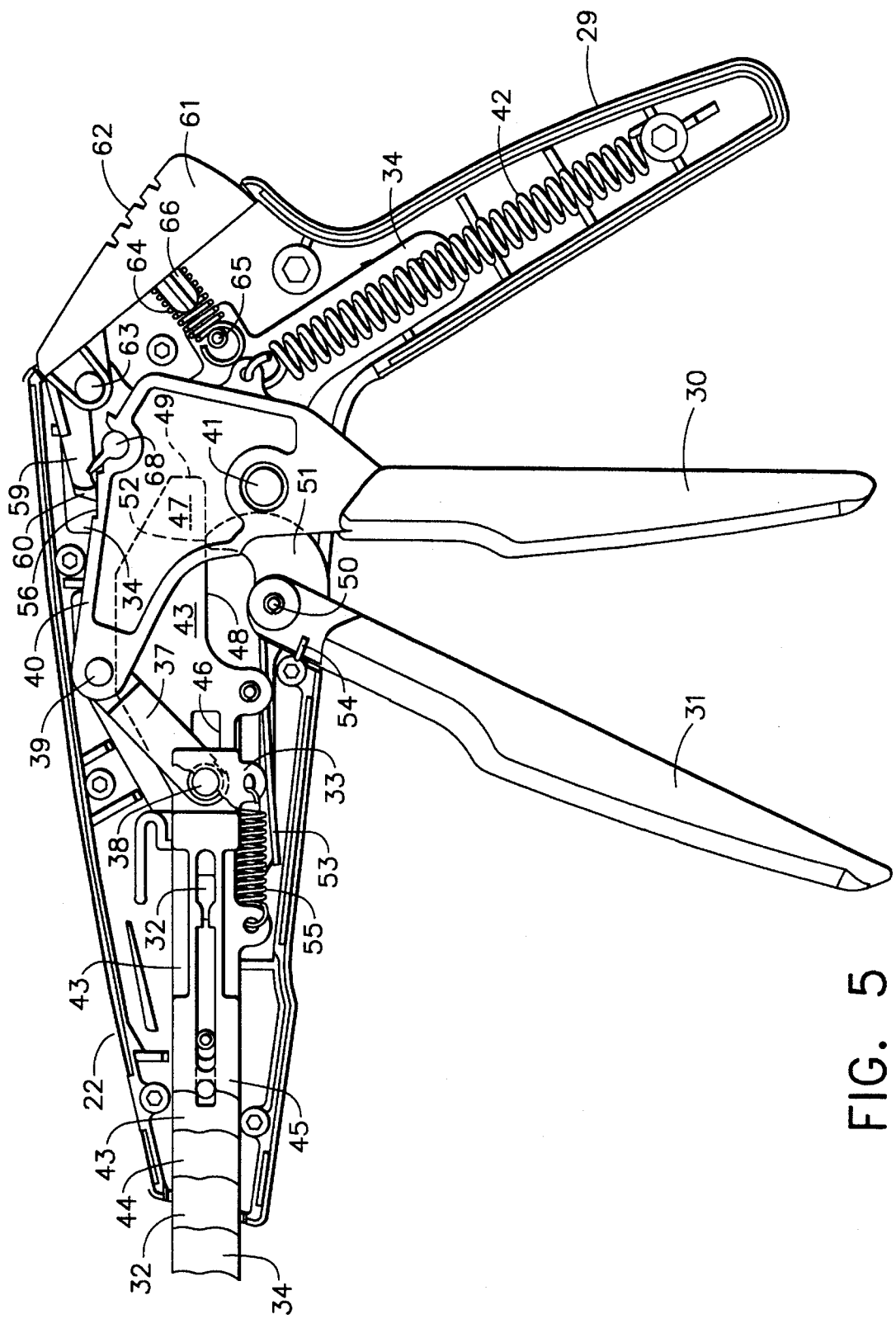
FIG. 5 is a truncated side elevation view of the frame portion of the linear stapler with the left hand shroud and the left hand hook removed to expose internal parts. Only the proximal end of the left hand closure plate is included in order to show the proximal half of the left hand spacer plate. The plates at the left end of the figure are cut off in succession for ease of identification.

Referring once again to FIG. 1 in combination with FIG. 5, a more detailed description of the components of the linear stapler can be provided. The clamping transmission assembly of the stapler includes right and left hand elongated closure plates 32 and 33, respectively, extending from the frame into the surgical fastening assembly of the end effector. The plates are positioned between the right and left hand hooks, 34 and 35, respectively. Right and left hand clamping links 36 and 37, respectively, are pivotally attached at the proximal ends of the right and left hand closure plates by a first integral clamping link pin 38. At the opposite end of the clamping links, the clamping links are pivotally attached to a second integral clamping link pin 39. The second integral clamping link pin connects the clamping links to a slotted clamping arm link 40. The slotted clamping arm link is pivotally mounted to the frame of the stapler at a clamping trigger pivot pin 41. The clamping trigger descends from the slotted clamping arm link for pivotal rotation about the clamping trigger pivot pin toward and away from the hand grip. A closure spring 42 housed within the hand grip of the frame is secured to the slotted clamping arm link to provide a desired resistance when the surgeon squeezes the clamping trigger toward the clamping grip, and to bias the clamping trigger toward the open position.

The components of the firing transmission assembly will now be described. The firing transmission assembly has an elongated firing bar 43 extending from the frame into the surgical fastening assembly of the end effector. The firing bar is positioned between the right and left hand closure plates, 32 and 33, respectively. In order to prevent undesirable deflection of the firing bar during firing, right and left hand spacer plates, 44 and 45, respectively, are positioned adjacent to each side of the firing bar between the firing bar and the right and left hand closure plates. The firing bar has a rectangular receiving slot 46 in that portion of the firing bar which is housed within the frame (see FIG. 5). The first integral clamping link pin 38 extends through the receiving slot. The firing bar also has a proximal end section 47. The underside of the proximal end section of the firing bar has a sliding surface 48. The proximal end section also has a terminal side engagement surface 49 extending from the sliding surface. The firing trigger is pivotally mounted to the frame by a firing trigger pivot pin 50 spaced from the clamping trigger pivot pin 41 so that each of the pivot pins pivots about mutually independent axes. The firing trigger includes an arcuate engagement link 51 extending from the firing trigger at the firing trigger pivot pin to an apex 52 which rests on the sliding surface of the proximal end section of the firing bar. Within the frame, the firing trigger is attached to first and second firing trigger spring arms, 53 and 54, respectively. The firing trigger spring arms support a torsion spring on the right half of the firing trigger (not shown). Finally, a firing bar return spring 55 is secured to the underside of the firing bar at that portion of the firing bar within the frame to bias the firing bar toward its unactuated position.

When the clamping trigger is squeezed toward the hand grip, the slotted clamping arm link 40 and the clamping links 36 and 37 move distally within the receiving slot 46 of the firing bar. This distal movement causes the closure plates 32 and 33 to correspondingly move distally. Likewise, the firing bar 43 concurrently moves distally with the closure plates because the first integral clamping link pin 38, to which the clamping links are attached, extends through the receiving slot in the firing bar.

The mechanism which defines the intermediate clamping detent position and the release of the clamping trigger from an actuated position to its original unactuated position will now be described in connection with FIG. 1 in combination with FIGS. 5–10. The top side of the slotted clamping arm link 40 has a clamp sliding surface 56 which displays an intermediate detent 57 and a clamping detent 58. A release pall 59 slides on the clamp sliding surface and may engage the intermediate and clamping detents. The release pall has a laterally extending pall lug (best seen in FIG. 1) at its distal end. The release pall is located within the frame, and it is integrally attached to a release button 61 situated exteriorly of the frame. The release button has a thumbrest 62, and the release button is pivotally attached to the frame by a release trunnion 63. The release button is biased outwardly from the frame, and therefore the release pall is biased downwardly toward the clamp sliding surface, by a release spring 64 which is mounted to the frame by a spring retention pin 65 and mounted to the release button by a button spring post 66. The slotted clamping arm link 40 has an arcuate recess 67 located between the intermediate and clamping detents. Sitting within this arcuate recess for rotational movement are a left hand toggle 68 integrally connected to a right hand toggle (the right hand toggle is not shown). Each toggle has a toggle arm 69 which is engageable with the pall lug 60. The pall lug has a concave proximal surface 70 to provide clearance between the toggle arm and the pall lug.

Figure 6:
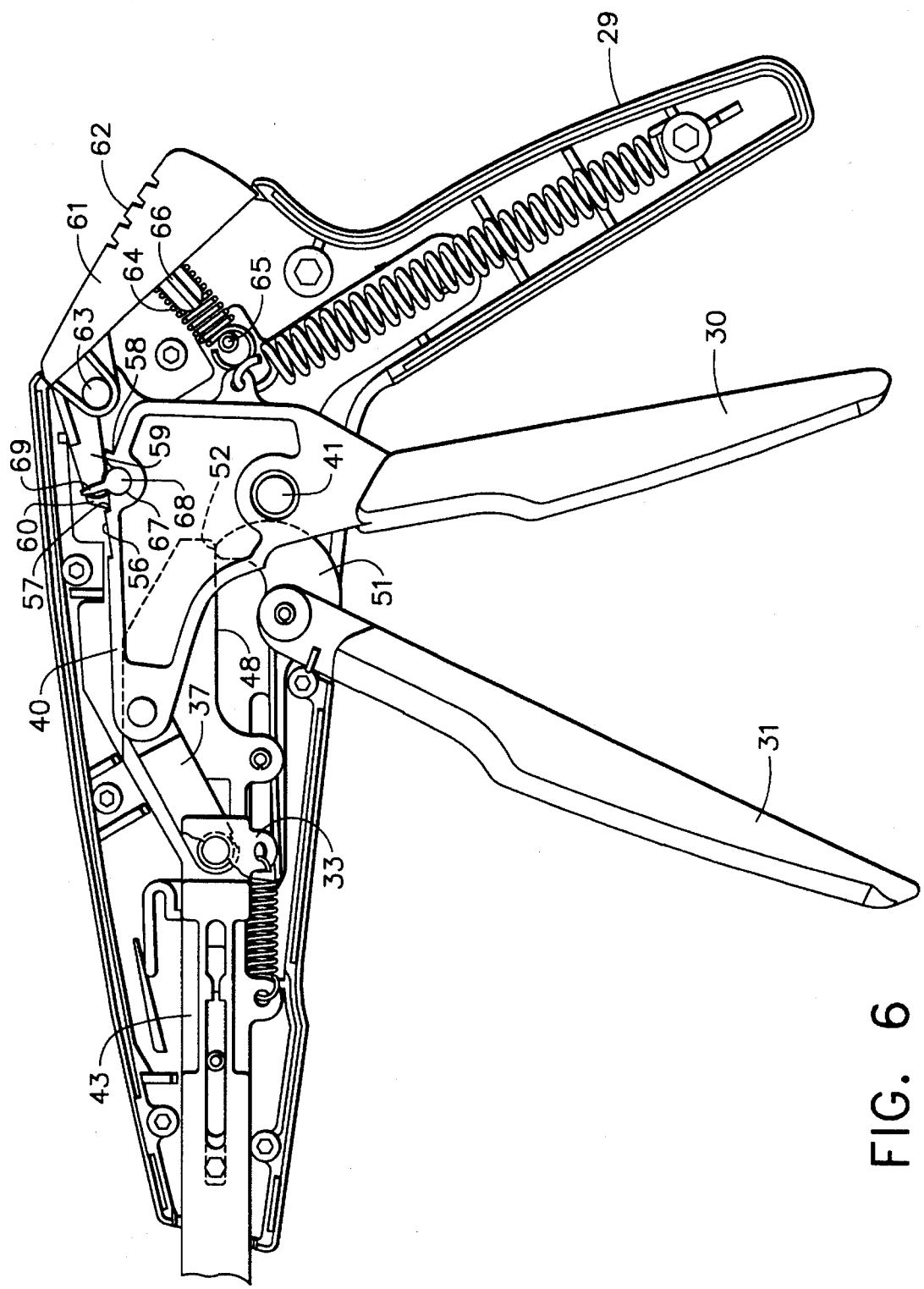
FIG. 6 is a truncated side elevation view as in FIG. 5 showing the clamping trigger of the linear surgical stapler in the detent or tissue retention position as shown in FIG. 2.

The operation of the clamping and firing mechanisms, and the intermediate clamping detent and release mechanism, will now be described more fully in connection with FIGS. 6–10. In FIG. 6, the clamping trigger 30 has been partially squeezed from its open, unactuated position illustrated in FIGS. 1 and 5. When the clamping trigger is partially squeezed, it pivots about the clamping trigger pivot pin 41 in a counterclockwise direction toward the hand grip. As it pivots, the slotted arm link 40 and closure plate clamping links 36 and 37 move forwardly, consequently moving the right and left hand closure plates, 32 and 33, and firing bar 43 distally. As the slotted arm link moves forwardly, the pall lug 60 of the release pall 59 slides on the clamp sliding surface 56. The pall lug 60 engages the distal ends of the toggle arms of the toggles, and consequently pivots the toggles in a clockwise direction. As the slotted arm link continues to move forwardly in response to the pivotal movement of the clamping trigger toward the hand grip, the pall lug 60 of the release pall 59 will eventually lodge into the intermediate detent 57. Once positioned in the intermediate detent, the closure spring is incapable of returning the clamping trigger to its original, unactuated position. The clamping trigger is now in its intermediate, partially closed position, to properly position and retain tissue between the cartridge and anvil, as shown in FIG. 2. In addition, as the right and left hand closure plates and firing bar move distally, the apex 52 of the arcuate firing trigger link 51 slides on the sliding surface 48 of the proximal end section of the firing bar.

Figure 7:
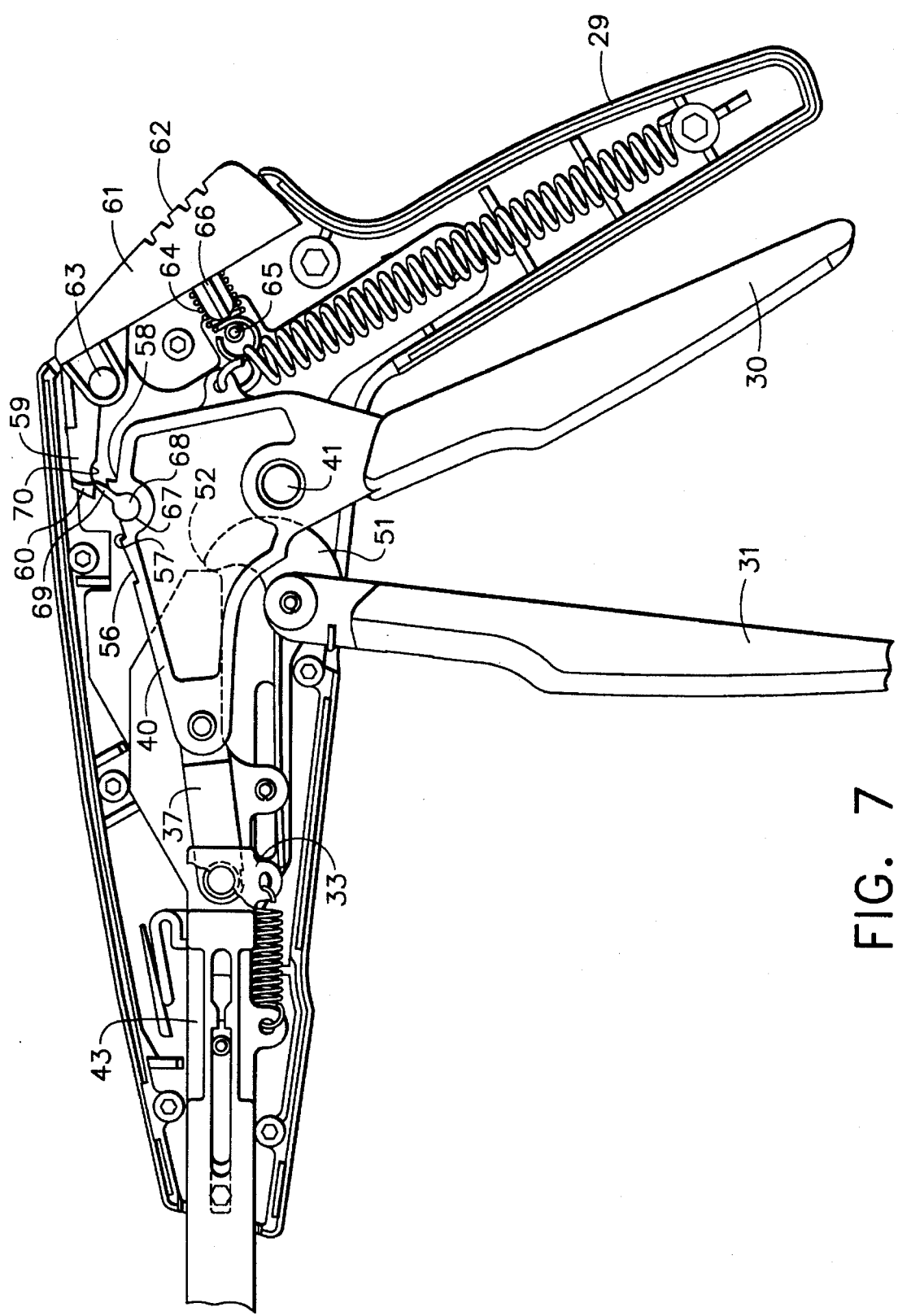
FIG. 7 is a truncated side elevation view as in FIG. 5 with the clamping trigger of the stapler bypassing the detent or tissue retention position as the clamping trigger is rotated.

Referring now specifically to FIG. 7, when the clamping trigger is squeezed toward the hand grip from the intermediate detent position, the toggle arms of the toggle disengage from the pall lug. Consequently, as the toggle continues to rotate in a clockwise direction, the release pall lug 60 rides up the toggle arms and with continued motion of the clamping trigger falls into the clamping detent 58. As the release pall rides up the toggle arm it rotates the release button clockwise around pivot 63. As the release pall 60 falls into clamping detent 58, it makes an audible clicking sound alerting the surgeon that clamping position has been reached. In addition, as the firing bar continues to move forwardly, the apex of the arcuate firing trigger link comes into contact with the side engagement surface 49 of the proximal end section of the firing bar. Consequently, the firing trigger is moving into a position where it can continue to move the firing bar distally to fire staples after the tissue has been fully clamped. When the apex of the arcuate firing trigger link moves into engagement with the engagement surface of the proximal end section, the firing trigger begins to pivotally rotate in a counterclockwise direction toward the hand grip in response to the action of a torsion spring on the right hand side of the trigger (torsion spring not shown). The firing trigger pivots independently of pivotal movement of the clamping trigger, but its pivotal rotation is blocked until the firing bar has moved distally to enable engagement of the firing trigger link with the terminal engagement surface of the firing bar.

Figure 8:
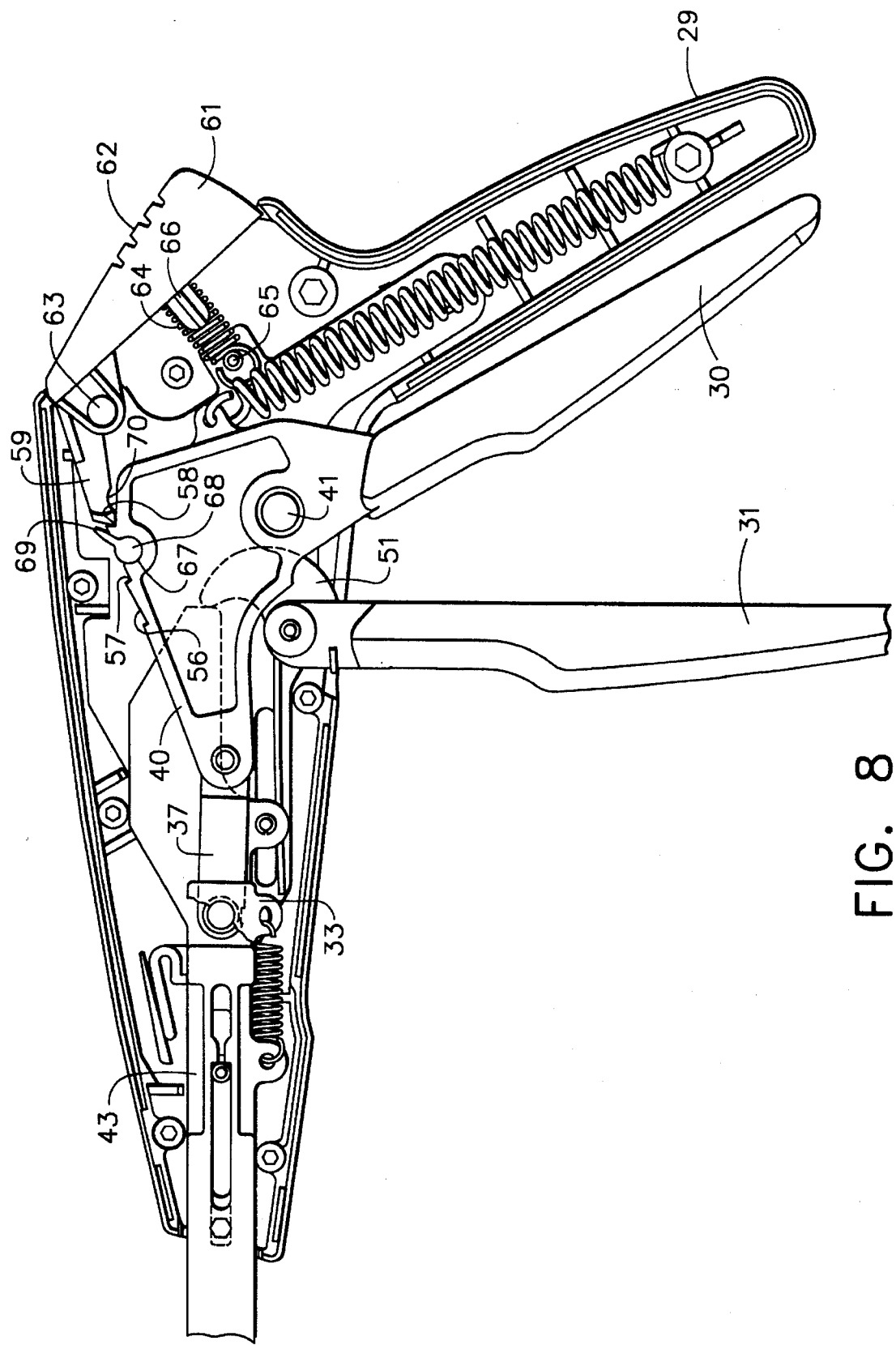
FIG. 8 is a truncated side elevation view as in FIG. 5 with the clamping trigger of the stapler in the clamped position as shown in FIG. 3 just prior to squeezing the firing trigger to fire staples.
Figure 9:
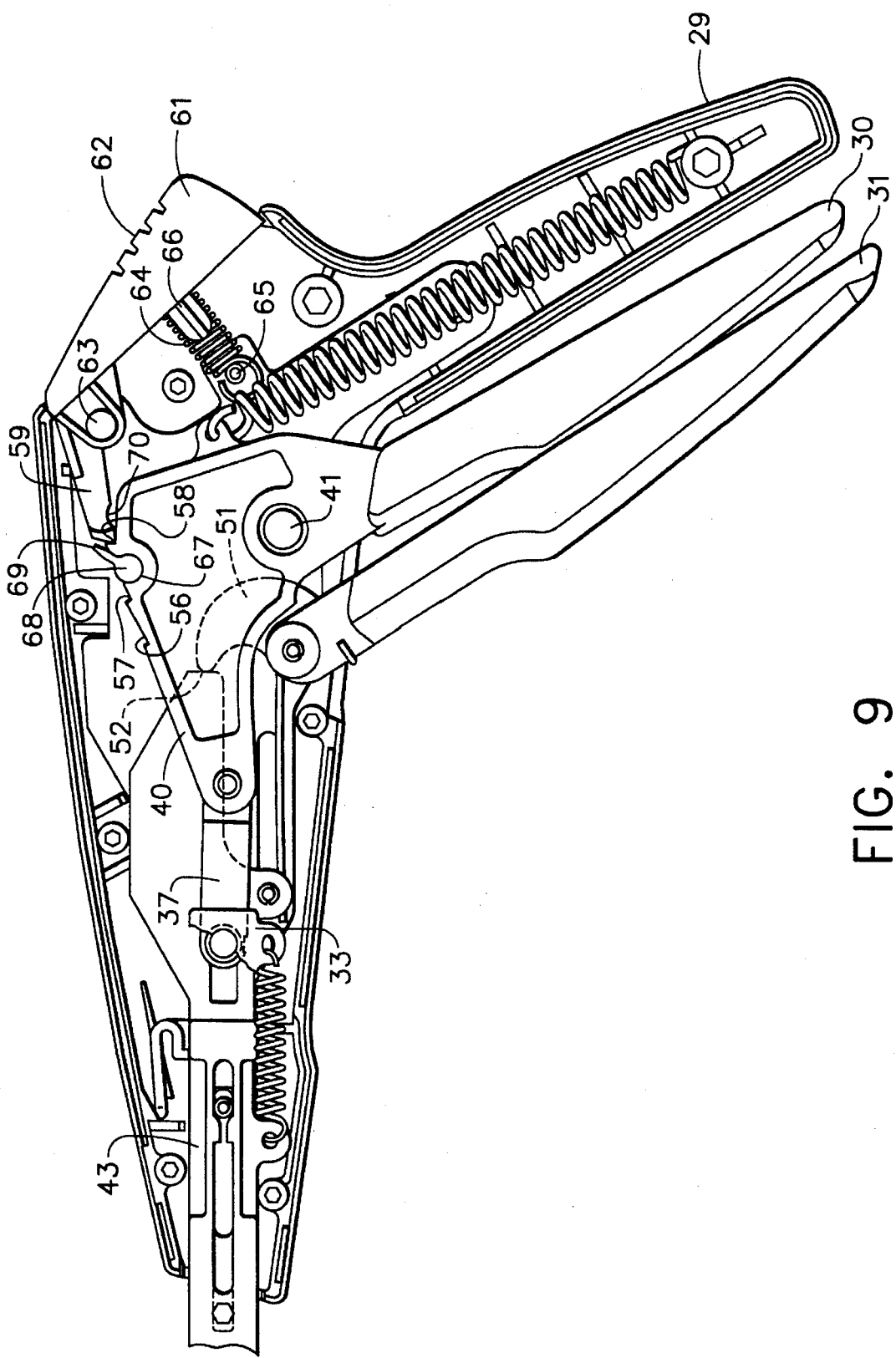
FIG. 9 is a truncated side elevation view as in FIG. 5 showing the firing trigger of the linear stapler in its fully fired position as shown in FIG. 4.

Turning specifically to FIG. 8, when the clamping trigger has been fully squeezed and it is adjacent the hand grip, the pall lug at the distal end of the release pall lodge into the clamping detent. In the clamping detent position, the tissue has been fully clamped between the cartridge and anvil and the closure spring is incapable of returning the clamping trigger to its original position. Therefore, the clamping trigger is retained in the position shown in FIG. 3. Concurrently with the counterclockwise motion of the clamping trigger, the firing trigger continues to rotate counterclockwise by the action of the torsion firing spring until the firing trigger is in a relatively vertical orientation with respect to the frame of the stapler. In the fully clamped position, the apex of the arcuate firing trigger link has fully engaged the engagement surface of the proximal end section of the firing bar, and therefore the firing trigger is in a position to further move the firing bar distally to fire staples into the tissue. As illustrated in FIG. 9, the firing trigger can be squeezed to pivotally rotate it toward the hand grip until it is positioned adjacent the clamping trigger. During the pivotal rotation of the firing trigger, the firing bar moves distally to fire the staples. In the position illustrated in FIG. 9, which is likewise the position shown in FIG. 4, the stapler has been fully fired.

Figure 10:
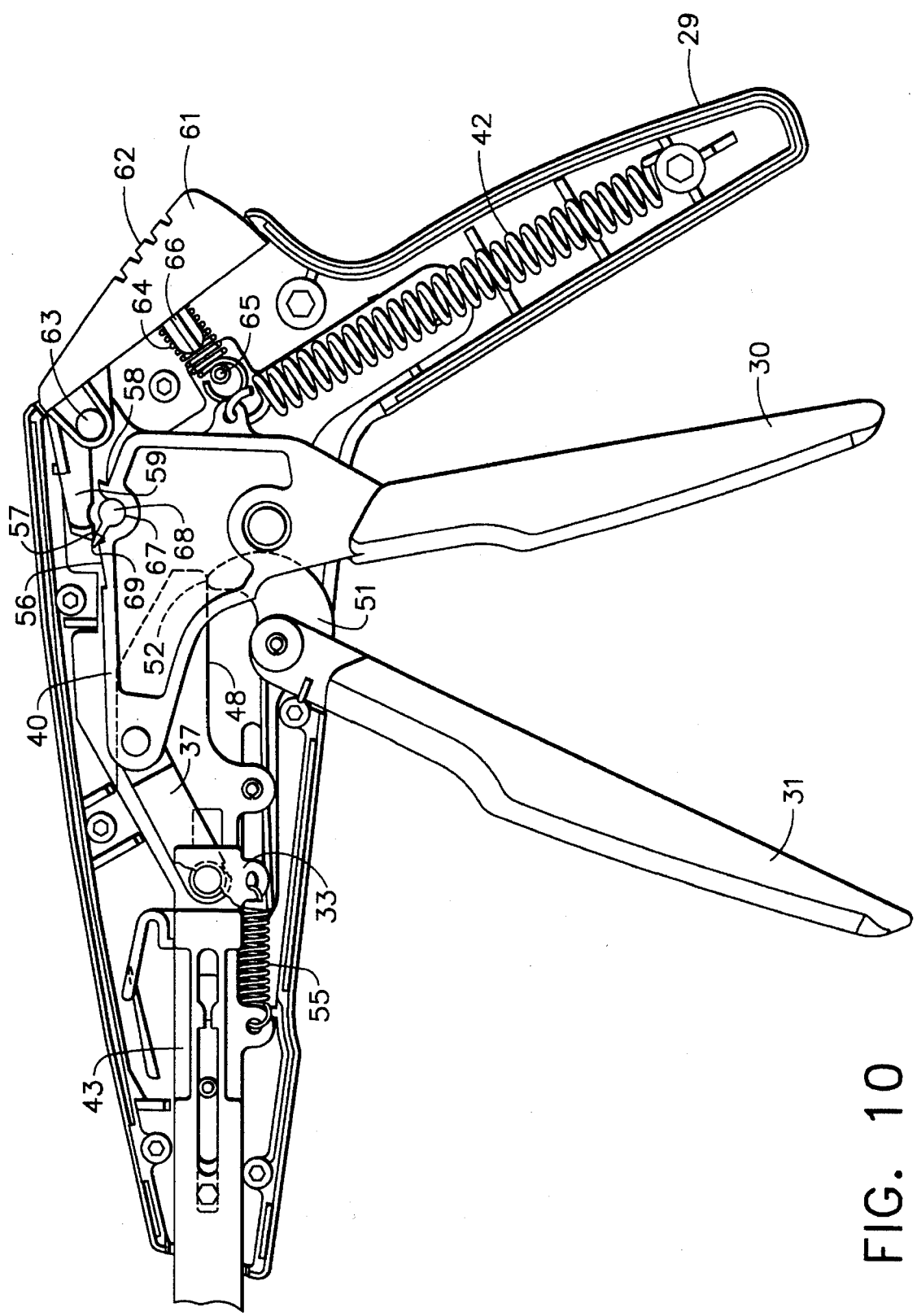
FIG. 10 is a truncated side elevation view as in FIG. 5 showing the clamping and firing triggers returning to their original positions.

Referring lastly to FIG. 10, when the surgeon depresses the release button 61, the release pall 59 pivots about the release trunnion 63 in a clockwise direction to dislodge the pall lug from the clamping detent position. As it is dislodged, the pall lug 60 rides on the toggle arms 69 to bypass the intermediate detent position 57 on clamp link 40. In this manner, the clamping and firing triggers can return to their original, unactuated positions in response to the bias created from the closure spring 42 and firing bar return spring 55. When the pall lug rides on the toggle arms of the toggles, the toggle arms rotate counterclockwise as the clamping and firing triggers rotate in a clockwise direction to return to their original unactuated positions. Therefore, the surgeon can release the clamping and firing triggers so that they can return to the positions illustrated in FIG. 5 without unnecessarily returning to the intermediate detent position.

Although this invention has been described in connection with its most preferred embodiment, numerous additional embodiments will become readily apparent to those skilled in this art. This description is intended to be illustrative only, and it is not intended to limit the scope or spirit of the claimed invention as it is defined in the claims which appear below. For example, although the invention has been specifically described in connection with a linear stapler, it is readily apparent that the invention is applicable to a multitude of various surgical instruments which are used for open and endoscopic surgical procedures.

What is claimed is:

1. A surgical instrument comprising:
    a) a frame at a first end of said instrument for gripping and manipulating said instrument, said frame having a body portion and a hand grip descending from said body portion thereof;
    b) an end effector at an opposite end of said instrument for performing a surgical procedure;
    c) a first trigger pivotally mounted to a first pivot pin within said body portion of said frame for pivotal rotation in a counterclockwise direction from an unactuated first trigger position spaced from said hand grip to a fully actuated first trigger position adjacent said hand grip;
    d) a first transmission assembly having proximal and distal ends, the proximal end of said first transmission assembly coupled to said first trigger and the distal end of said first transmission member coupled to said end effector, wherein:
        (i) when said first trigger is pivotally rotated in the counterclockwise direction from said unactuated first trigger position toward said hand grip, said first transmission assembly moves distally so as to cause said end effector to perform a first surgical function in the surgical procedure;
    e) a second trigger pivotally mounted to a second pivot pin within said body portion of said frame for pivotal rotation in a counterclockwise direction from an unactuated second trigger position spaced from said first trigger to a fully actuated second trigger position adjacent said first trigger, wherein said second pivot pin is spaced from said first pivot pin, said pivotal rotation of said second trigger is independent of said pivotal rotation of said first trigger, and said first trigger is positioned between said second trigger and said hand grip; and
    f) a second transmission assembly having proximal and distal ends, the proximal end of said second transmission assembly being engagable with said second trigger and the distal end of the said second transmission assembly being engagable with said end effector, wherein:
        (i) when said first trigger is positioned in said unactuated first trigger position, the proximal end of said second transmission assembly blocks the pivotal rotation of said second trigger in a counterclockwise direction;
        (ii) when said first trigger is pivotally rotated in the counterclockwise direction from said unactuated first trigger position toward said hand grip, said second transmission assembly moves distally concurrently with said first transmission assembly so as to prevent blocking of said pivotal rotation of said second trigger; and
        (iii) when said first trigger is positioned in said fully actuated first trigger position and said second trigger is pivotally rotated in a counterclockwise direction toward said first trigger, said second transmission assembly continues to move distally so as to cause said end effector to perform a second surgical function in the surgical procedure.

2. The surgical instrument of claim 1 wherein when said first trigger has pivotally rotated to said fully actuated first trigger position, said second trigger has rotated from said unactuated position toward said hand grip.

3. The surgical instrument of claim 2 wherein said second trigger is attached to a second trigger link which contacts the proximal end of said second transmission assembly.

4. The surgical instrument of claim 3 wherein the proximal end of said second transmission assembly has a slide surface and a side engagement surface, and said second trigger link slides on said slide surface when first trigger is pivotally rotated from said unactuated first trigger position toward said hand grip, and said second trigger link engages said side engagement surface when said first trigger is pivotally rotated to said fully actuated first trigger position.

5. The surgical instrument of claim 4 wherein said first trigger is attached to an arm link having an arm sliding surface with an intermediate detent and a final detent.

6. The surgical instrument of claim 5 further comprising a release pall pivotally mounted to said body portion of said frame, said pall biased toward said arm sliding surface for sliding movement thereon as said first trigger is pivotally rotated.

7. The surgical instrument of claim 6 wherein when said first trigger is pivotally rotated from said unactuated first trigger position in a counterclockwise direction, said pall slides on said arm sliding surface and becomes lodged in said intermediate detent, and said first trigger is retained in an intermediate actuated position between said unactuated first trigger position and said actuated first trigger position.

8. The surgical instrument of claim 7 further comprising a toggle rotatably secured to said arm sliding surface and positioned between said intermediate detent and said final detent, said toggle having a toggle arm extending therefrom, said toggle arm being engagable with said pall when said first trigger is positioned in said unactuated first trigger position.

9. The surgical instrument of claim 8 wherein when said first trigger is pivotally rotated from said unactuated first trigger position to said intermediate actuated position, said pall causes said toggle arm to rotate in a first direction.

10. The surgical instrument of claim 9 wherein when said first trigger is pivoted from said intermediate actuated position to said fully actuated first trigger position, said pall initially rides over said final detent on said toggle arm, and then disengages from said arm to become lodged at said final detent wherein said first trigger is retained in said fully actuated first trigger position.

11. The surgical instrument of claim 10 further comprising a pall release button resiliently attached to said body portion of said frame and connected to said release pall, wherein when said pall is lodged in said final detent, and said release button is depressed, said button counterbiases said pall from said arm sliding surface to dislodge said pall from said final detent so as to enable said first trigger to pivotally rotate from said fully actuated first trigger position toward said unactuated first trigger position, and wherein when said first trigger pivotally rotates toward said unactuated first trigger position, said pall causes said toggle arm to rotate in a reverse direction and said pall rides over said intermediate detent so as to enable said first trigger to return to said unactuated first trigger position.

12. The surgical instrument of claim 1 wherein said end effector includes a surgical fastening assembly.

13. The surgical instrument of claim 12 wherein said assembly has a staple cartridge with a tissue-contacting surface thereon, and an anvil with a staple-forming surface thereon, said surfaces moveable toward and away from each other for positioning and clamping tissue therebetween.

14. The surgical instrument of claim 13 wherein said first transmission assembly includes at least one closure element for moving said cartridge and anvil toward each other, and said second transmission assembly includes an elongated firing bar for firing staples from said cartridge onto said anvil.

15. The surgical instrument of claim 14 wherein said first trigger is a clamping trigger and said second trigger is a firing trigger.

16. The surgical instrument of claim 15 wherein said first transmission assembly has a pair of spaced-apart, elongated closure plates separated by said firing bar.

17. The surgical instrument of claim 16 further comprising a tissue retaining pin engagable when said closure plates move distally to protrude from said cartridge through said anvil.

18. The surgical instrument of claim 17 wherein when said first trigger is pivotally rotated from said unactuated first trigger position toward said hand grip, said cartridge moves toward said anvil, and said retaining pin protrudes from said cartridge through said anvil.

19. The surgical instrument of claim 18 wherein said instrument is a linear stapler.

* * * * *